United States Patent
Rittsteiger et al.

(10) Patent No.: US 10,343,975 B2
(45) Date of Patent: *Jul. 9, 2019

(54) COUPLING OF DISTILLATIVE PURIFICATION WITH A PARTIAL CONDENSER FOR PRE-PURIFICATION OF ISOPHORONEDIAMINE

(71) Applicant: Evonik Degussa GmbH, Essen (DE)

(72) Inventors: Anne Rittsteiger, Olfen (DE); Alexander Martin Rüfer, Recklinghausen (DE); Guido Streukens, Wuppertal (DE); Stephan Kohlstruk, Gladbeck (DE); Matthias Orschel, Münster (DE); Matthias Mendorf, Dortmund (DE); Jorn Walscharts, Edegem (BE); Axel Hengstermann, Senden (DE); Anja Müller, Dortmund (DE)

(73) Assignee: Evonik Degussa GmbH, Essen (DE)

( * ) Notice: Subject to any disclaimer, the term of this patent is extended or adjusted under 35 U.S.C. 154(b) by 43 days.

This patent is subject to a terminal disclaimer.

(21) Appl. No.: 15/473,892

(22) Filed: Mar. 30, 2017

(65) Prior Publication Data

US 2017/0298003 A1   Oct. 19, 2017

(30) Foreign Application Priority Data

Apr. 19, 2016  (EP) .................................... 16165898

(51) Int. Cl.
  *C07C 209/84*  (2006.01)
  *B01D 3/10*  (2006.01)
  (Continued)

(52) U.S. Cl.
  CPC ............ *C07C 209/84* (2013.01); *B01D 3/103* (2013.01); *B01D 3/143* (2013.01); *B01D 5/006* (2013.01);
  (Continued)

(58) Field of Classification Search
  None
  See application file for complete search history.

(56) References Cited

U.S. PATENT DOCUMENTS

| 3,352,913 A | 11/1967 | Schmitt et al. |
| 8,198,481 B2 | 6/2012 | Kuppinger et al. |

(Continued)

FOREIGN PATENT DOCUMENTS

| CN | 104230721 A | 12/2014 |
| EP | 2649042 A1 | 10/2013 |

(Continued)

OTHER PUBLICATIONS

Luyben, Ind. Eng. Chem. Res. 2004, 43, 6416-6429.*

*Primary Examiner* — Clinton A Brooks
(74) *Attorney, Agent, or Firm* — Philip P. McCann; Nexsen Pruet, PLLC

(57) ABSTRACT

A process for fine purification of isophoronediamine (IPDA), including producing IPDA by aminating hydrogenation of isophorone nitrile in the presence of at least ammonia, hydrogen, a a hydrogenation catalyst and optionally further additions to obtain a crude IPDA, and subjecting the crude IPDA to a fine purification via two vacuum distillation columns, wherein in the first vacuum distillation column the removal of any remaining relatively low-boiling byproducts is effected and in the second vacuum distillation column the IPDA is obtained in pure form as tops and thus separated from the organic residues, and wherein the first vacuum distillation column has vacuum distillation column has a partial condenser fitted to it.

15 Claims, 2 Drawing Sheets

(51) Int. Cl.
*B01D 3/14* (2006.01)
*B01D 5/00* (2006.01)
*C07C 211/36* (2006.01)

(52) U.S. Cl.
CPC ........ *C07C 211/36* (2013.01); *C07C 2601/14* (2017.05)

(56) References Cited

U.S. PATENT DOCUMENTS

| | | |
|---|---|---|
| 8,252,120 B2 | 8/2012 | Nordhoff et al. |
| 8,293,941 B2 | 10/2012 | Kuppinger et al. |
| 8,362,299 B2 | 1/2013 | Hengstermann et al. |
| 8,481,784 B2 | 7/2013 | Kuppinger et al. |
| 8,877,976 B2 | 11/2014 | Lettmann et al. |
| 8,895,683 B2 | 11/2014 | Kuppinger et al. |
| 9,085,506 B2 | 7/2015 | Galle et al. |
| 2013/0253226 A1* | 9/2013 | Galle .................... C07C 209/26 564/445 |
| 2013/0261341 A1* | 10/2013 | Lettmann .............. C07C 211/36 564/448 |
| 2018/0029971 A1* | 2/2018 | Rittsteiger ............... B01D 3/10 |

FOREIGN PATENT DOCUMENTS

| | | |
|---|---|---|
| WO | 2012076315 A1 | 6/2012 |
| WO | 2012126869 A1 | 9/2012 |
| WO | 2016120235 A1 | 8/2016 |

* cited by examiner

COUPLING OF DISTILLATIVE PURIFICATION WITH A PARTIAL CONDENSER FOR PRE-PURIFICATION OF ISOPHORONEDIAMINE

This application claims the benefit of European Application No. 16165898.4 filed on Apr. 19, 2016, the disclosure of which is expressly incorporated herein by reference.

BACKGROUND

The invention relates to the fine purification of isophoronediamine (IPDA) using a two-stage column setup comprising a partial condenser.

The production of IPDA by aminating hydrogenation of isophorone nitrile (IPN) is known and has been described numerous times.

In the simplest case (U.S. Pat. No. 3,352,913), IPN is reacted in the presence of hydrogen and of an excess of ammonia over a cobalt catalyst. IPN and ammonia initially react with elimination of water to form isophorone nitrile imine, IPNI, which is subsequently hydrogenated to IPDA.

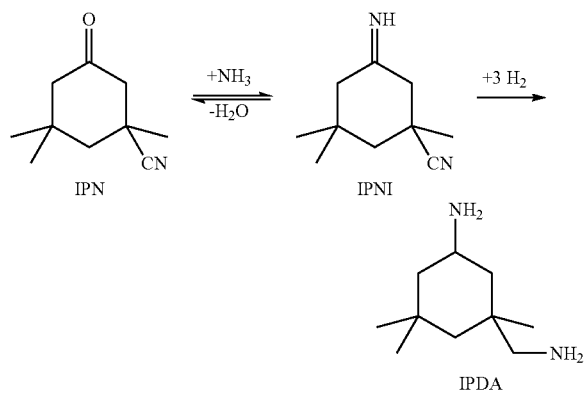

FIG. 1

In addition, processes for producing isophoronediamine are known from CN 104230721A, EP 2649042 A and WO 2012126869A.

In EP 2 649 042A isophoronediamine is produced from isophorone nitrile in a one- or two-stage reaction. Isophorone nitrile is initially iminated with ammonia to afford isophorone nitrile imine. Said isophorone nitrile imine is hydrogenated to afford isophoronediamine in the second step. The purification that follows the reaction is likewise divided into two steps. The low boilers are initially removed in a plurality of distillation columns, said low boilers including hydrogen, inert gases, ammonia and low-boiling impurities (low boiler removal). In a final step the pure isophoronediamine is then obtained via two vacuum distillation columns. The first column in turn serves to remove any remaining relatively low-boiling byproducts. In the second column the isophoronediamine is obtained in pure form as tops and thus separated from the organic residues (high boilers).

SUMMARY

The present invention has for its object to provide a simple process for fine purification of isophoronediamine having reduced energy requirements in the form of heating and cooling power.

It was found that, surprisingly, the use of an additional partial condenser in the first vacuum distillation makes it possible to reduce the energy requirements for the fine distillation of isophoronediamine.

The invention provides a process for fine purification of crude isophoronediamine from the production of isophoronediamine by aminating hydrogenation of isophorone nitrile in the presence of at least ammonia, hydrogen, a hydrogenation catalyst and optionally further additions and in the presence or absence of organic solvents to obtain a crude isophoronediamine, characterized in that the crude isophoronediamine is subjected to a fine purification via two vacuum distillation columns, wherein in the first vacuum distillation column the removal of any remaining relatively low-boiling byproducts is effected and in the second vacuum distillation column the isophoronediamine is obtained in pure form as tops and thus separated from the organic residues, and wherein the first vacuum distillation column has a partial condenser fitted to it.

BRIEF DESCRIPTION OF THE DRAWINGS

Reference will now be made to the accompanying drawings wherein like reference characters designate the same or similar parts throughout the several views, and wherein.

DETAILED DESCRIPTION

Figure 1:
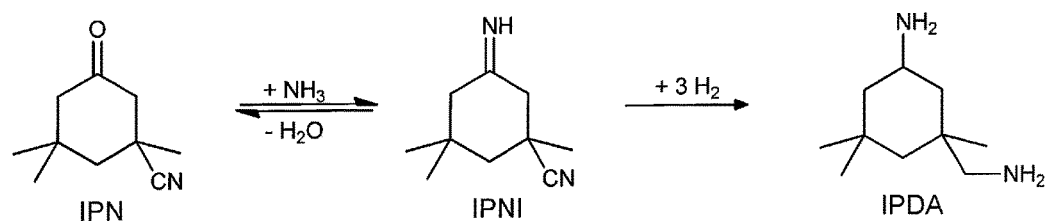
FIG. 1 is a chemical reaction showing the chemical reaction of isophorone nitrile (IPN) to make isophoronediamine (IPNA)
Figure 2:
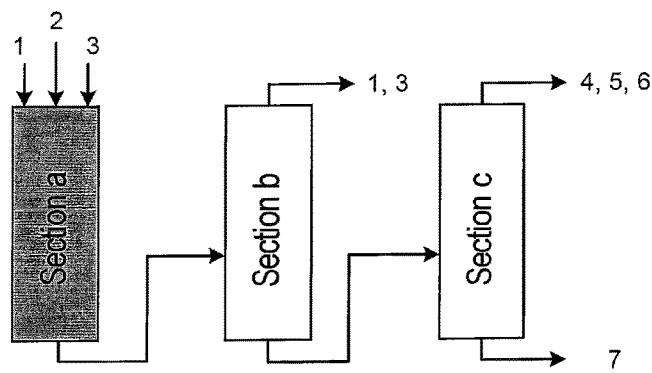
FIG. 2 is a block diagram of the IPNA chemical reaction of FIG. 1 including step a—reductive amination reaction, b distillative ammonia removal and c fine distillation of IPA.

This entire process for producing pure IPDA is divided into three sections (see FIG. 2). In section a the reaction is effected by aminating hydrogenation of isophorone nitrile in a single- or multi-stage process in the presence of at least ammonia, hydrogen and a catalyst. In section b the distillative removal of ammonia and hydrogen to obtain crude IPDA is affected. The distillation may be performed in one or more columns. In section c the fine purification of crude IPDA is effected by distillative removal of IPDA, water, low boilers and high boilers. The fine purification is performed in two columns.

The crude IPDA generally has the following composition in weight % (wt %):

| | |
|---|---|
| IPDA | 75-100 wt % |
| Water | 0-15 wt % |
| Low boilers | 0-6 wt % |
| High boilers | 0-6 wt % |

Low boilers are defined as byproducts from the production process having a lower boiling point than IPDA. High boilers are defined as byproducts from the production process having a higher boiling point than IPDA.

Figure 3:
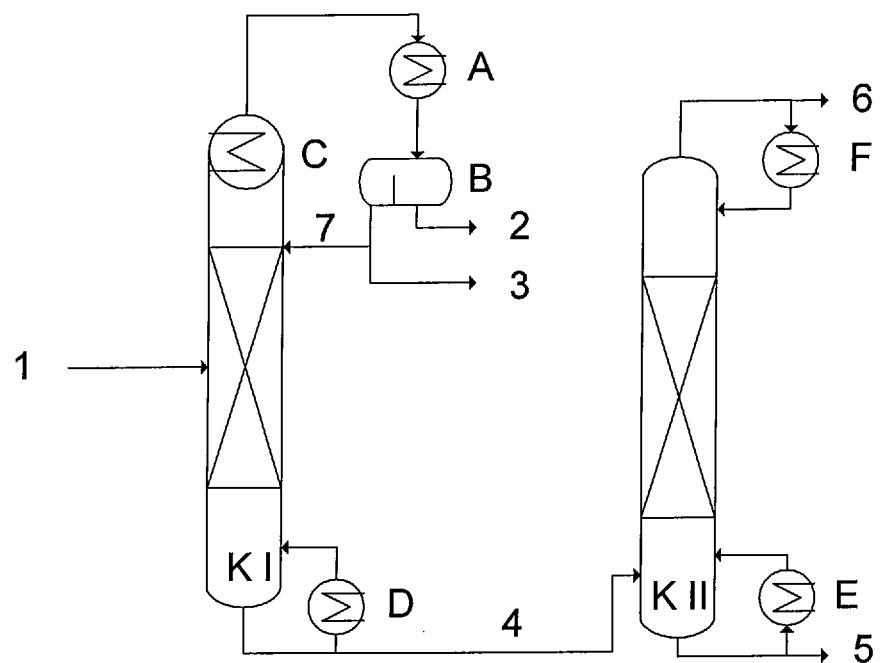
FIG. 3 is a schematic perspective view of the column setup with partial condenser for fine distillation of IPNA.

The crude IPDA I is initially passed into the first vacuum distillation column, see FIG. 3. The partial condenser is installed at the top of the first vacuum distillation column and may be attached either inside the vacuum distillation column or outside the distillation column. The vapor stream is thus pre-cooled and consequently partly condensed in the partial condenser. The condensed liquid is used as return stream in the vacuum distillation column. The uncondensed vapor stream is subsequently fully condensed and divided into an organic phase 3 and an aqueous phase 2 in a second condenser, wherein the organic phase 3 is partly used as reflux for the first vacuum distillation column (phase 7). The other part and the aqueous phase serve as discharge for low boilers and water. The IPDA leaves the vacuum distillation column as bottoms stream and is sent to a second vacuum distillation column for removal of the high boilers, the pure IPDA being obtained here at the top of the second vacuum distillation column.

The partial condenser is operated under the following conditions:

| | |
|---|---|
| Temperature | 40-120° C. |
| Pressure | 10-200 mbar |

The employed 1st vacuum distillation column has the following parameters:

| | |
|---|---|
| Pressure | 10-200 mbar |
| Bottoms temperature | 80-200° C. |
| Theoretical plates | 10-80 |

The composition of the feed stream (crude IPDA II) from the 1st vacuum distillation column into the 2nd vacuum distillation column has the following composition:

| | |
|---|---|
| IPDA | 90-100 wt % |
| High boilers | 0-10 wt % |

The employed 2nd vacuum distillation column has the following parameters:

| | |
|---|---|
| Pressure | 10-200 mbar |
| Tops temperature | 80-200° C. |
| Theoretical plates | 5-50 |

The purity of the pure isophoronediamine shall be at least 98 wt %.

EXAMPLES

Example 1: Comparative Example

The distillation was simulated using Aspen Plus. In the comparative example a setup composed of two vacuum distillation columns was chosen. At the top of the first distillation column a decanter was used to separate the two liquid phases, only the organic phase being used as reflux for the vacuum distillation column. The first vacuum distillation column had 36 theoretical plates and the second vacuum distillation column had 15 theoretical plates, with reflux-to-feed ratios of 1.1 (first vacuum distillation column) and 1.4 (second vacuum distillation column). The column pressure of the first vacuum distillation column was set to 110 mbar and that of the second vacuum distillation column was set to 80 mbar.

The feed stream employed at the following composition in weight % (wt %):

| | |
|---|---|
| IPDA | 88.6 wt % |
| Water | 9.1 wt % |
| Low boilers | 1.2 wt % |
| High boilers | 1.1 wt % |

In the first vacuum distillation column the removal of the low boilers and of the water was effected at a bottoms temperature of 168° C. and a tops temperature of 95° C. The feed stream from the first vacuum distillation column into the second vacuum distillation column thus had the following composition:

| | |
|---|---|
| IPDA | 98.7 wt % |
| High boilers | 1.3 wt % |

In the second vacuum distillation column the fine purification of IPDA was effected at a bottoms temperature of 187° C. and a tops temperature of 159° C. A purity of 99.95 wt % was achieved. The total loss of IPDA over the 2 vacuum distillation column system was 0.2 wt %

At a chosen feed mass flow of 2160 kg per hour
the heating power required was: 1184 kW
and the cooling power required was: 1232 kW.

Example 2: Inventive Vacuum Distillation Column Setup

The distillation was simulated using Aspen Plus. In the inventive example a setup composed of two vacuum distillation columns was chosen. At the top of the first vacuum distillation column a decanter was used to separate the two liquid phases. In addition, a partial condenser was installed upstream of the decanter. In this apparatus the vapor stream was first partially condensed and then added to the vacuum distillation column as reflux. The remaining vapor stream was subsequently fully condensed and separated into the two liquid phases via the decanter. The organic phase was likewise used as reflux for the vacuum distillation column. The first vacuum distillation column had 36 theoretical plates and the second vacuum distillation column had 15 theoretical plates, with reflux-to-feed ratios of 1.1 (first vacuum distillation column) and 1.4 (second vacuum distillation column). The column pressure of the first vacuum distillation column was set to 110 mbar and that of the second vacuum distillation column was set to 80 mbar.

The feed stream employed at the following composition in weight % (wt %):

| | |
|---|---|
| IPDA | 88.6 wt % |
| Water | 9.1 wt % |
| Low boilers | 1.2 wt % |
| High boilers | 1.1 wt % |

In the first vacuum distillation column the removal of the low boilers and of the water was effected at a bottoms temperature of 168° C., a tops temperature of 117° C. and a partial condenser temperature of 74° C. The feed stream from the first vacuum distillation column into the second vacuum distillation column thus had the following composition:

| | |
|---|---|
| IPDA | 98.7 wt % |
| High boilers | 1.3 wt % |

In the second vacuum distillation column the fine purification of IPDA was effected at a bottoms temperature of 187° C. and a tops temperature of 159° C. A purity of 99.95 wt % was achieved. The total loss of IPDA over the 2 column system was 0.2 wt %

At a chosen feed mass flow of 2160 kg per hour
the heating power required was: 1006 kW
and the cooling power required was: 1048 kW.

In the inventive distillation setup with the installed partial condenser the required heating and cooling powers were 15% lower than in the comparative setup.

The invention claimed is:

1. A process for fine purification of isophoronediamine (IPDA), pure isophoronediamine, comprising the steps of:
   (a) producing isophoronediamine by aminating hydrogenation of isophorone nitrile in the presence of at least ammonia, hydrogen, a hydrogenation catalyst and further additions to obtain a crude isophoronediamine;
   (b) distillative removing the ammonia and hydrogen from the isophoronediamine of step (a) to obtain the crude isophoronediamine; and
   (c) purifying the crude isophoronediamine of step (b) via a first vacuum distillation column comprising a partial condenser and a vapor stream, and a second vacuum distillation column by distillative removing of isophoronediamine, water, low boilers and high boilers from the crude isophoronediamine to make a fine purification,
   wherein the vapor stream is pre-cooled and partly condensed in the partial condenser to form a condensed liquid, which is used as return stream in the first vacuum distillation column, and
   wherein the isophoronediamine leaves the first vacuum distillation column as a bottoms stream, wherein the bottoms stream is sent to the second vacuum distillation column wherein high boilers are removed to obtain the purity of the pure isophoronediamine is at least 98 wt % as tops.

2. The process according to claim 1, wherein the crude isophoronediamine generally comprises the following composition in weight % (wt %) based on the weight of the crude isophoronediamine:

| IPDA | 75-100 wt %; |
|---|---|
| Water | 0-15 wt %; |
| Low boilers | 0-6 wt %; and |
| High boilers | 0-6 wt %. |

3. The process according to claim 2, wherein the uncondensed vapor stream in the first vacuum distillation column is fully condensed and divided into an organic phase and an aqueous phase in a second condenser, wherein the organic phase is partly used as reflux for the first vacuum distillation column.

4. The process according to claim 2, wherein IPDA leaves the first vacuum distillation column as bottoms stream and is sent to a second vacuum distillation column for removal of the high boilers.

5. The process according to claim 2, wherein the pure IPDA is obtained at the top of the second vacuum distillation column.

6. The process according to claim 2, wherein the partial condenser is operated under the following conditions:

| Temperature | 40-120° C.; and |
|---|---|
| Pressure | 10-200 mbar. |

7. The process according to claim 2, wherein the employed first vacuum distillation column comprises the following parameters:

| Pressure | 10-200 mbar; |
|---|---|
| Bottoms temperature | 80-200° C.; and |
| Theoretical plates | 10-80. |

8. The process according to claim 1, wherein the purity of the pure isophoronediamine is at least 99.95 wt %.

9. The process according to claim 1, wherein the uncondensed vapor stream in the first vacuum distillation column is fully condensed and divided into an organic phase and an aqueous phase in a second condenser, wherein the organic phase is partly used as reflux for the first vacuum distillation column.

10. The process according to claim 1, wherein IPDA leaves the first vacuum distillation column as bottoms stream and is sent to a second vacuum distillation column for removal of the high boilers.

11. The process according to claim 1, wherein the pure IPDA is obtained at the top of the second vacuum distillation column.

12. The process according to claim 1, wherein the partial condenser is operated under the following conditions:

| Temperature | 40-120° C.; and |
|---|---|
| Pressure | 10-200 mbar. |

13. The process according to claim 1, wherein the employed first vacuum distillation column comprises the following parameters:

| Pressure | 10-200 mbar; |
|---|---|
| Bottoms temperature | 80-200° C.; and |
| Theoretical plates | 10-80. |

14. The process according to claim 1, wherein the composition of the feed stream from the first vacuum distillation column into the second vacuum distillation column (crude IPDA II) comprises the following composition (wt %) based on the weight of the crude isophoronediamine:

| IPDA | 90-100 wt %; and |
|---|---|
| High boilers | 0-10 wt %. |

15. The process according to claim 1, wherein the employed second vacuum distillation column comprises the following parameters:

| Pressure | 10-200 mbar; |
|---|---|
| Tops temperature | 80-200° C.; and |
| Theoretical plates | 5-50. |

* * * * *